US011298519B2

(12) United States Patent
Josephy et al.

(10) Patent No.: US 11,298,519 B2
(45) Date of Patent: Apr. 12, 2022

(54) USE OF CARDIAC ASSIST DEVICE TO IMPROVE KIDNEY FUNCTION

(71) Applicant: Abiomed, Inc., Danvers, MA (US)

(72) Inventors: Noam Josephy, Danvers, MA (US); Jerald Wayne Curran, Danvers, MA (US); Randi Parks, Danvers, MA (US)

(73) Assignee: Abiomed, Inc., Danvers, MA (US)

( * ) Notice: Subject to any disclaimer, the term of this patent is extended or adjusted under 35 U.S.C. 154(b) by 96 days.

(21) Appl. No.: 16/406,896

(22) Filed: May 8, 2019

(65) Prior Publication Data
US 2020/0237987 A1 Jul. 30, 2020

Related U.S. Application Data

(60) Provisional application No. 62/668,689, filed on May 8, 2018.

(51) Int. Cl.
*A61M 60/135* (2021.01)
*A61M 60/148* (2021.01)
(Continued)

(52) U.S. Cl.
CPC ........ *A61M 60/135* (2021.01); *A61M 60/148* (2021.01); *A61M 60/422* (2021.01); *A61M 60/857* (2021.01); *A61M 2205/3344* (2013.01); *A61M 2210/1082* (2013.01); *A61M 2210/125* (2013.01)

(58) Field of Classification Search
CPC .. A61M 1/125; A61M 1/1008; A61M 1/1031; A61M 1/122; A61M 60/135; A61M 2205/3344; A61M 2210/1082; A61M 2210/125

See application file for complete search history.

(56) References Cited

U.S. PATENT DOCUMENTS 6,136,025 A 10/2000 Barbut et al.
9,474,840 B2 * 10/2016 Siess ...................... A61B 5/686
(Continued)

FOREIGN PATENT DOCUMENTS

WO 2015177793 A2 11/2015

OTHER PUBLICATIONS

International Search Report and Written Opinion for International Application No. PCT/US2020/031861 dated Jul. 20, 2020 (7 pages).

*Primary Examiner* — Mallika D Fairchild
*Assistant Examiner* — Naveed R. Kolia
(74) *Attorney, Agent, or Firm* — Botos Churchill IP Law LLP

(57) ABSTRACT

Systems and methods for improving kidney function. A first mechanical circulatory support system (MCS) is introduced in a patient's heart, and a second mechanical circulatory support system is introduced in a patient's inferior vena cava or renal vein. The second mechanical circulatory support system is operated while the first mechanical circulatory support system is operating. A renal parameter is monitored during. Combined operation of the two mechanical circulatory support systems results in a change in renal parameter, e.g. pressure drop in the renal vein, indicating an improvement in kidney function. Once the renal parameter is determined to be below a target threshold, operation of the second mechanical circulatory support device is stopped.

18 Claims, 3 Drawing Sheets

(51) Int. Cl.
*A61M 60/422* (2021.01)
*A61M 60/857* (2021.01)

(56) References Cited

U.S. PATENT DOCUMENTS

| | | | |
|---|---|---|---|
| 2007/0208291 A1* | 9/2007 | Patel | A61M 1/3613 604/4.01 |
| 2016/0022890 A1* | 1/2016 | Schwammenthal | A61F 2/07 600/17 |
| 2017/0112986 A1 | 4/2017 | Heuring et al. | |

* cited by examiner

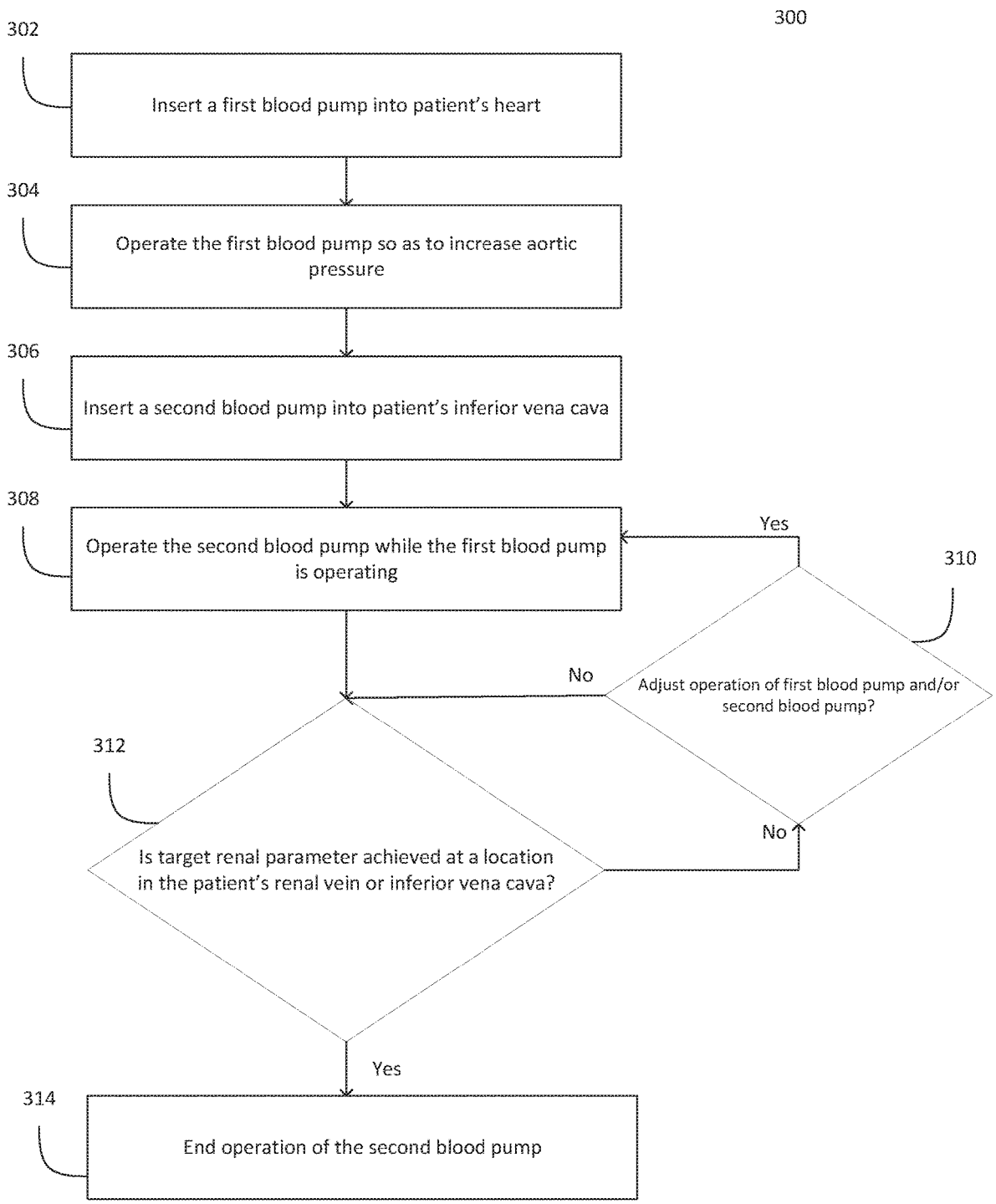

USE OF CARDIAC ASSIST DEVICE TO IMPROVE KIDNEY FUNCTION

CROSS-REFERENCE TO RELATED APPLICATIONS

This application claims priority to U.S. Patent Application Ser. No. 62/668,689, filed May 8, 2018, entitled "Use of Cardiac Assist Device to Adjust Kidney Autoregulation," the entire contents of which are hereby incorporated by reference in their entirety, including Exhibit A.

BACKGROUND

The kidneys play a central role in controlling arterial fluid pressure in the body. They modulate renal output by changing the output of water (diuresis) and also by changing the output of salt (natriuresis). The modulation is reflected in a renal output curve (FIG. 1), where urinary output varies according to arterial pressure. In normal conditions, the kidney can autoregulate itself, increasing or decreasing urine output and renal blood flow according to increases or decreases in blood pressure or flow rate, or changes in salt concentration. However, autoregulation may be impaired by injury or other changes in kidney function. For example, impaired kidney function can increase the arterial pressure, as would an increase in the level of water and salt in the circulation. Conversely, heart failure or coronary disease can dramatically reduce cardiac output, which in turn reduces blood flow to the renal artery and impairs urine output.

Many people suffer from acute kidney disease, kidney failure, and other kidney disorders. Some kidney disorders are believed to be caused or exacerbated by contrast media, dyes and other media used during CT scans, angiograms, and other investigative procedures. Those conditions include, for example, contrast induced nephropathy and nephrogenic systemic fibrosis, or general kidney toxicity. Patients with diabetes, heart, blood and other vascular diseases may have increased susceptibility to such disorders. A frequent indication of kidney disorder is reduced kidney glomerular filtration rate (GFR) and kidney output, with an acute condition known as oliguria (acute reduction in urine output).

In particular when undergoing surgery, patients with compromised cardiac function and/or preexisting renal conditions may need to be put on cardiac bypass. Their heart, as a result of the stress of surgery, release stressors through their body. A type and amount of stressors released by the heart can vary depending on a length or nature of the surgery (e.g. CABG, valve replacement, valve repair, etc.). Patients may have their kidney output monitored as an indicator of recovery either during or immediately after surgery. For example, an increase in creatinine or a decrease in filtration rate may be monitored to gauge patient recovery. Current systems such as ECMO which provide a flat line pressure, do not improve kidney function and may instead damage kidneys by placing them into a high pressure state. Monitoring of kidney output as an indicator of recovery is particularly important for high-risk cardiac patients (e.g. STEMI, CS, PCI) who also frequently suffer from acute kidney disease, failure or disorders.

It would be desirable to provide improved methods and systems that can improve kidney functionality, particularly in cases of vascular disease. In particular, it would be desirable to provide a system or method that can provide one or more of improved kidney output, reduced kidney toxicity of various agents, and controlled kidney autoregulation. It would be desirable to provide a system or method that can increase flow into a kidney, to increase urine output and the processing of undesirable stressors out of the body. It would also be desirable to provide a system or method that can monitor a renal parameter to determine whether flow into the kidney is sufficient such that increased flow into the kidney is no longer necessary.

SUMMARY

Methods and systems are provided herein for addressing one or more of the foregoing problems. Kidney output can be increased by increasing blood flow through the kidney. Blood flow through the kidney can be modulated by unloading the heart and maintaining or increasing arterial pressure upstream of a kidney; maintaining or decreasing venous pressure downstream of the kidney, or a combination of both—selected to maintain or increase a pressure gradient across the kidney. At least one advantage of unloading the heart and increasing arterial pressure upstream of a kidney is an increased release of one or more humoral factors that operates on kidney receptors (at or near the renal artery or glomerulus or any of the nephron components) or on other receptors in vascular tissue. The increase in these humoral factors binding to the kidney advantageously increases the kidney's ability to process undesirable stressors out of the body. Similarly, at least one advantage of decreasing venous pressure downstream of the kidney is to increase blood flow (including humoral factors) through the kidney, thereby increasing kidney output. Methods and systems provided herein also address renal monitoring, by monitoring a renal parameter to determine whether the second blood pump can be turned off. For example, by monitoring a pressure gradient across the kidney, or a venous pressure drop in the renal vein, at least one advantage is the ability to determine once a patient has sufficiently regained kidney function, such that the second blood pump can be turned off. In one example, the first and second blood pumps can be one of the blood pumps known as Impella® pumps, and the first blood pump can be applied to the left or right side of the heart (or both) for example by using any of the techniques identified in Exhibit A.

In some implementations, a method is provided for modulating kidney function in a patient. Steps in the method include inserting a first mechanical assist device, e.g. a first blood pump, into the patient's heart and operating the first blood pump so as to increase aortic pressure. For example, the blood pump can be introduced into a left heart or a right heart of the patient. In left ventricular applications, an inlet of the pump is positioned in the left ventricle, and an outlet of the pump is in the aorta. Alternatively, the blood pump can be inserted into a left atrium, such that an inlet of the pump is in the left atrium and an outlet of the pump is in the left ventricle. Alternatively, the blood pump can be inserted in any position which unloads the heart and maintains or increases cardiac output. The method also comprises inserting a second mechanical assist device, e.g. a second blood pump, into an inferior vena cava of the patient and operating the second blood pump while the first blood pump is operating. For example, the second blood pump is placed near or within the inferior vena cava, or within the inlet of the inferior vena cava, or within the renal vein. The second blood pump's inlet may be placed within the junction between the patient's renal vein and inferior vena cava. In another example, the second blood pump is configured to partially occlude the inferior vena cava, such that operation of the second blood pump creates a pressure drop upstream of the second blood pump inlet (between the pump and the kidney, including within the renal vein). In these implementations, operation of the first and second blood pumps achieves a target pressure drop at a location in the patient's renal vein or inferior vena cava. The first and second blood pumps can thus be operated simultaneously—the first pump on the arterial side of the kidney increases pressure upstream of the kidney, while the second pump located distal (downstream) of the kidney unloads the kidney and thereby decreases pressure in the renal vein. In other adaptations, one of the blood pumps is operated continuously, and the other of the blood pumps is selectively turned on and off to achieve the target pressure drop. The first blood pump and the second blood pumps may also be operated at different speeds, for differing amounts of time. For example, the first blood pump may be operated at about 40,000 rpms for up to 6 hours, whereas the second blood pump may be operated at 30,000 rpms for about 3 hours. Alternatively, both first and second blood pumps may be operated similar speeds over the same time periods.

At least one advantage of using the first blood pump is unloading the heart's left or right ventricle (or both), or left or right atria (or both), thereby improving not only blood circulation through the renal artery but also stimulating the release of one or more humoral factors that operates on kidney receptors (at or near the renal artery or glomerulus or any of the nephron components) or on other receptors in vascular tissue. Such stimulation increases kidney output, helping to manipulate and maintain kidney autoregulation, and also helps protect the kidney from toxicity and injury. Deploying and operating the first blood pump can be used to unload the left ventricle, thereby reducing left ventricular pressure (and left atrial pressure) and volume, or unload the right ventricular and reduce right ventricular pressure (and right atrial pressure) and volume, or both.

At least one advantage of unloading the ventricle by pumping blood from the ventricle into the artery and carrying blood away from the heart (either the aorta or the pulmonary artery) is a general increase in arterial pressure, which increases pulsatility in the vasculature and increases the flow of blood into the renal artery and kidneys, thereby increasing the glomerular filtration rate. Another advantage of operating the first pump, e.g. an Impella® pump, in the patient's heart, is increasing diastolic pressure—the kidneys receive significant blood flow by diastolic pressure—without constantly maintaining the kidneys in a high pressure state. Yet another advantage of unloading of the heart, e.g. with an Impella® pump, is to upregulate the production of one or more humoral factors in the cardiac tissue (or arterial tissue) and release of such one or more factors into the circulation. A majority of humoral factors are produced within the left atrium of the heart—unloading the heart decompresses the left atrium and boosts humoral factor production (e.g. ANP Production). Humoral factors flowing to a kidney and/or other organs' receptor(s) will actuate the kidney or other organs(s) receptors and stimulate an increase in that organ's function. The humoral factors flowing to the kidney will actuate the kidney receptors and stimulate an increase in urine exiting the kidney. For example, released humoral factors bind to kidney receptors or other organ receptor. When the humoral factors reach the renal artery (and the nephrons of the kidney), the humoral factors bind to one or more kidney receptors and thereby actuate the afferent and/or the efferent arterioles directly of vis-à-vis the mesangial cells in the glomerulus to thereby increase or decrease the renal blood flow. Increasing renal blood flow in turn increases or decreases, or maintains, the glomerular filtration rate even if the renal perfusion pressure changes. In addition, or alternatively, humoral factors may activate the kidney tubules' walls to excrete and/or absorb or reabsorb glucose, salt or other electrolytes into the urine, whereupon water from the surrounding vasculature and tissue passively follows the change in electrolytes levels in the urine, causing a respective modulation (increase/decrease/maintenance in the urine output and urine content) even when facing changing renal perfusion pressure and changes in blood electrolytes, glucose and trace elements. Receptors in the kidney that are implicated by this effect can include atrial natriuretic peptide (ANP), Brain Natriuretic Peptide (BNP), NT-proBNP, catecholamine receptors, adenosine receptors, angiotension receptors (AT1, AT2), prostaglandin receptors, alpha keto-glutorate receptors, glutamate receptors, to name a few. For example, kidney receptors are disposed within the kidney's nephron or tubule or medulla or cortex.

In some implementations, operating the first blood pump in the heart maintains or increases arterial pressure in the renal artery. In other implementations, operating the second blood pump in the inferior vena cava maintains or decreases renal vein pressure. For example, in one implementation, the first blood pump is operated to increase arterial pressure while the second blood pump is operated to decrease renal vein pressure. In another example, the first blood pump is operated to maintain arterial pressure, while the second blood pump is operated to decrease renal vein pressure. In yet another example, the first blood pump is operated to increase arterial pressure, while the second blood pump is operated to maintain renal vein pressure.

In some implementations, the target pressure drop at the location in the patient's renal vein or inferior vena cava increases blood flow through the kidney and increases kidney output. For example, the target pressure drop is between about 4 mmHg and about 8 mmHg. In another example, the target pressure drop is between about 5 mmHg and about 7 mmHg. In one example, the target pressure drop is about 6 mmHg. The target pressure drop and the time period necessary to achieve this target pressure drop may vary depending on a baseline of a particular patient, and a patient's condition. For example, for a particular patient a maximum achievable pressure drop may be lower than the target pressure drop (e.g. 2 mmHg). In another example, for another patient, the target pressure drop is achievable, but may require a longer time period operating the first and second blood pumps to achieve. The target pressure drop and time period necessary to achieve it may also vary depending on the type of mechanical circulatory support devices used—for example an Impella® pump providing increased diastolic pressure would require less time than an intra-aortic balloon pump, or other type of mechanical circulatory system.

In some implementations, the target pressure drop corresponds to a blood pressure drop across the kidney. In one example, the target pressure drop is between 85 mmHg and 95 mmHg. The target pressure drop and the time period necessary to achieve the target pressure drop may vary depending on a baseline of a particular patient, and a patient's condition. The target pressure drop and time period necessary to achieve it may also vary depending on the type of mechanical circulatory support devices used—for example an Impella® pump providing increased diastolic pressure would require less time than an intra-aortic balloon pump, or other type of mechanical circulatory system.

In some implementations, combined operation of the first and second blood pumps flows humoral factors to the kidney receptors to stimulate an increase in urine exiting the kidney.

In some implementations, the first blood pump (e.g. an Impella® pump) comprises a pump motor, along with a pump housing distal of the pump motor. The pump housing surrounds the rotor, and a cannula extends distal of the pump housing. In some examples, an atraumatic extension extends distally from the cannula. For example, the atraumatic extension is pigtail-shaped.

In some implementations, the second blood pump comprises a pump motor, along with a pump housing distal of the pump motor. The pump housing surrounds a rotor and a cannula extends distal of the pump housing. In some examples, an atraumatic extension extends distally from the cannula. For example, the atraumatic extension is pigtail-shaped.

In some implementations, the second pump is positioned inside the inferior vena cava such that a distal tip of the atraumatic extension extends to a point inside the inferior vena cava adjacent to the outlet of the renal vein. For example, the distal tip of the atraumatic extensions extends between 0-2 centimeters of the point where the renal vein connects to the inferior vena cava. At least one benefit of the distal tip extending between 0-2 centimeters of the point where the renal vein connects to the inferior vena cava is the ability to stabilize the pump's inlet at a desired location adjacent the renal vein.

In other implementations, a system for improving kidney function comprises a first mechanical assist device configured to unload a patient's heart, and a second mechanical assist device configured to decrease renal vein pressure. For example, the first mechanical assist device is configured to unload at least one heart ventricle, at least one heart atrium, or at least one atrium and ventricle, or both atria and both ventricles of the patient's heart. The first and second mechanical assist devices are configured to achieve a target pressure drop in the renal vein when operated simultaneously. In one example, one or both of the mechanical assist devices are blood pumps. In another example, the second mechanical assist device is a balloon pump.

In some implementations, the system for improving kidney function also includes a controller (e.g. an Automated Impella Controller®) configured to receive an arterial pressure from the first mechanical assist device, and a venous pressure from the second mechanical assist device. The controller determines whether a pressure drop in the renal vein is near a target pressure drop in the renal vein, and controls an adjustment in the operation of at least one of the first mechanical assist device and second mechanical assist device. In one example, the adjustment in operation helps achieve the target pressure drop in the renal vein. In another example, when the target pressure drop has been achieved, the adjustment in operation includes turning off one or both of the mechanical assist devices. In one example, the system includes two controllers (e.g. two Automated Impella Controllers®), each controller being associated with one mechanical assist device (e.g. an Impella® pump) and receiving data from their respective mechanical assist device.

In some implementations, the target pressure drop is configured to increase urine production. For example, the controller is configured to operate one or more of the mechanical assist devices at respective rates that increase blood flow from the heart and stimulate production of at least one humoral factor that binds to a kidney receptor or another organ receptor to stimulate and/or modulate urine production and urinary fluid composition from the kidneys.

In some implementations, the second mechanical assist device comprises a pump motor and a pump housing distal of the pump motor. The pump housing surrounds a rotor, and a cannula extends distal of the pump housing. In an example, the second mechanical assist device also comprises an anchoring device, configured to anchor the second mechanical assist device to the inferior vena cava while the second mechanical assist device is operating. The anchoring device surrounds a portion of the cannula. The anchoring device can be selectively actuated. For example, the anchoring device is a balloon. The balloon can be inflated to partially occlude the inferior vena cava. Alternatively, the anchoring device comprises deployable arms which engage with the wall of the inferior vena cava. For example, the anchoring device is a nitinol self-expanding cage.

In some implementations, the second mechanical assist device is positioned with an inlet positioned at a location where the renal vein connects to the inferior vena cava.

In some implementations, each of the first and second mechanical assist devices comprise a pressure sensor to measure an arterial pressure and a venous pressure, respectively. In one example, a pressure sensor is integrated with each of the first and second mechanical assist devices. For example, the first and second mechanical assist devices are Impella® pumps comprising a differential pressure sensor or an optical pressure sensor. In another example, a separate pressure sensor wire or Swan-Ganz catheter is inserted along with each of the first and second mechanical assist devices. In yet another example, one of the mechanical assist devices includes an integrated sensor, while the other of the mechanical assist devices does not—and is instead used in combination with a separate pressure sensor wire, or Swan-Ganz catheter.

In some implementations, when both first and second mechanical assist devices are operating simultaneously, a difference between the measured venous pressure and the measured arterial pressure increases. For example, the difference between the measured venous pressure and the measured arterial pressure increases by about 1%. In another example, the difference increases by about 5%.

In yet another implementation, a method for improving kidney function in a patient, comprises inserting a first blood pump into the patient's heart and operating the first blood pump. The method further comprises inserting a second blood pump into an inferior vena cava of the patient, and while the first blood pump is operating, operating the second blood pump. The method also comprises monitoring a renal parameter, and when the renal parameter has reached a target level, ending operation of the second blood pump. For example, the target level for the renal parameter is a function of aortic pressure. For example, the renal parameter is creatinine level or ANP concentration in the blood or renal vein pressure. In one example, the target level for the renal vein pressure is less than 15 mmHg. In another example, the renal parameter is a pressure drop across the kidney.

In some implementations, the renal parameter is determined by measuring arterial pressure and measuring venous pressure, and calculating a pressure difference between the measured arterial pressure and the measured renal vein pressure. In some implementation, the method for improving kidney function in a patient also includes determining the calculated pressure difference has reached a threshold value.

In some implementations, the first blood pump is in communication with a first controller and the second blood pump is in communication with a second controller. For example, the first and second controllers are Automated Impella Controllers® (AICs). In one implementation, the first controller and the second controller communicate to determine the pressure difference between the measured arterial pressure and the measured renal vein pressure.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 3 shows an illustrative method disclosed herein.

DETAILED DESCRIPTION

To provide an overall understanding of the systems, method, and devices described herein, certain illustrative embodiments will be described. Although the embodiments and features described herein are specifically described for use with an intracardiac heart pump system, it will be understood that all the components and other features outlined below may be combined with one another in any suitable manner, and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices.

The systems, methods and devices described herein provide for improvement of kidney function by maintaining or increasing arterial pressure upstream of the kidney, maintaining or decreasing venous pressure downstream of the kidney, or a combination of both to achieve increased blood flow through the kidney and in turn increased kidney output.

Figure 1:
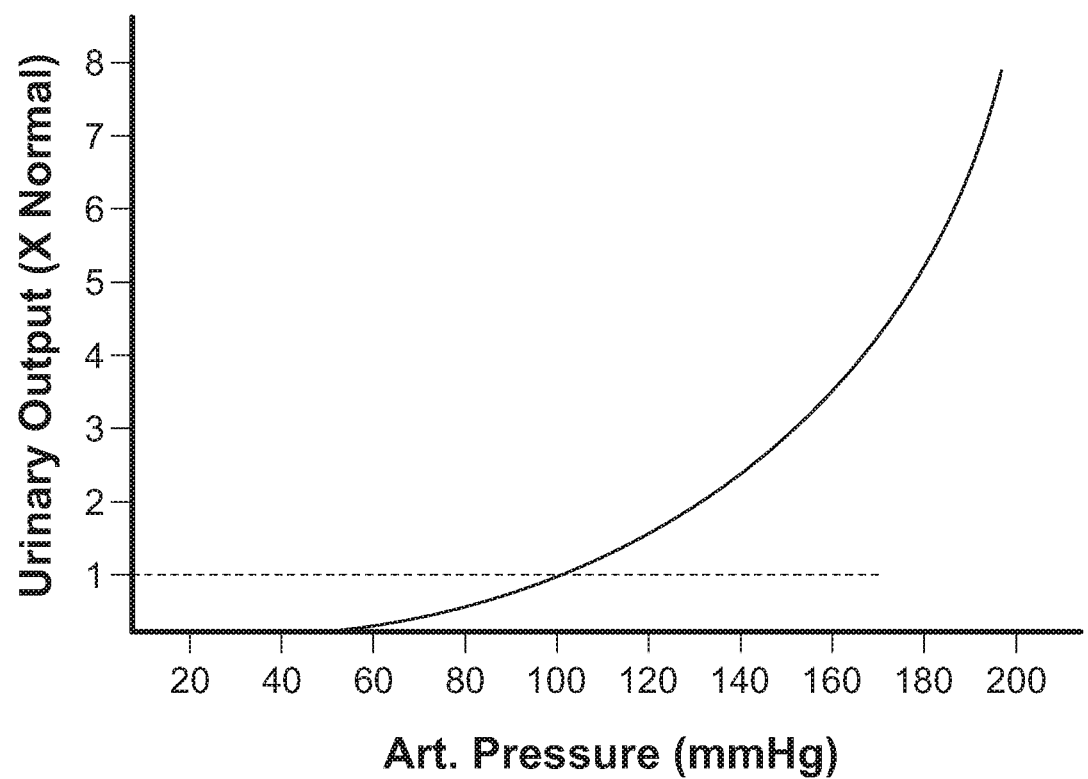
FIG. 1 shows an illustrative renal output curve where urinary output varies according to arterial pressure.

FIG. 1 shows an illustrative renal output curve where urinary output varies according to arterial pressure. For example, as discussed above, a higher arterial pressure increases blood flow to the kidney. Arterial blood carries humoral factors to the kidney, such that a higher arterial pressure results in an increased amount of humoral factors reaching the kidney and binding to receptors on the kidney, in turn increasing kidney function and urinary output.

Figure 2:
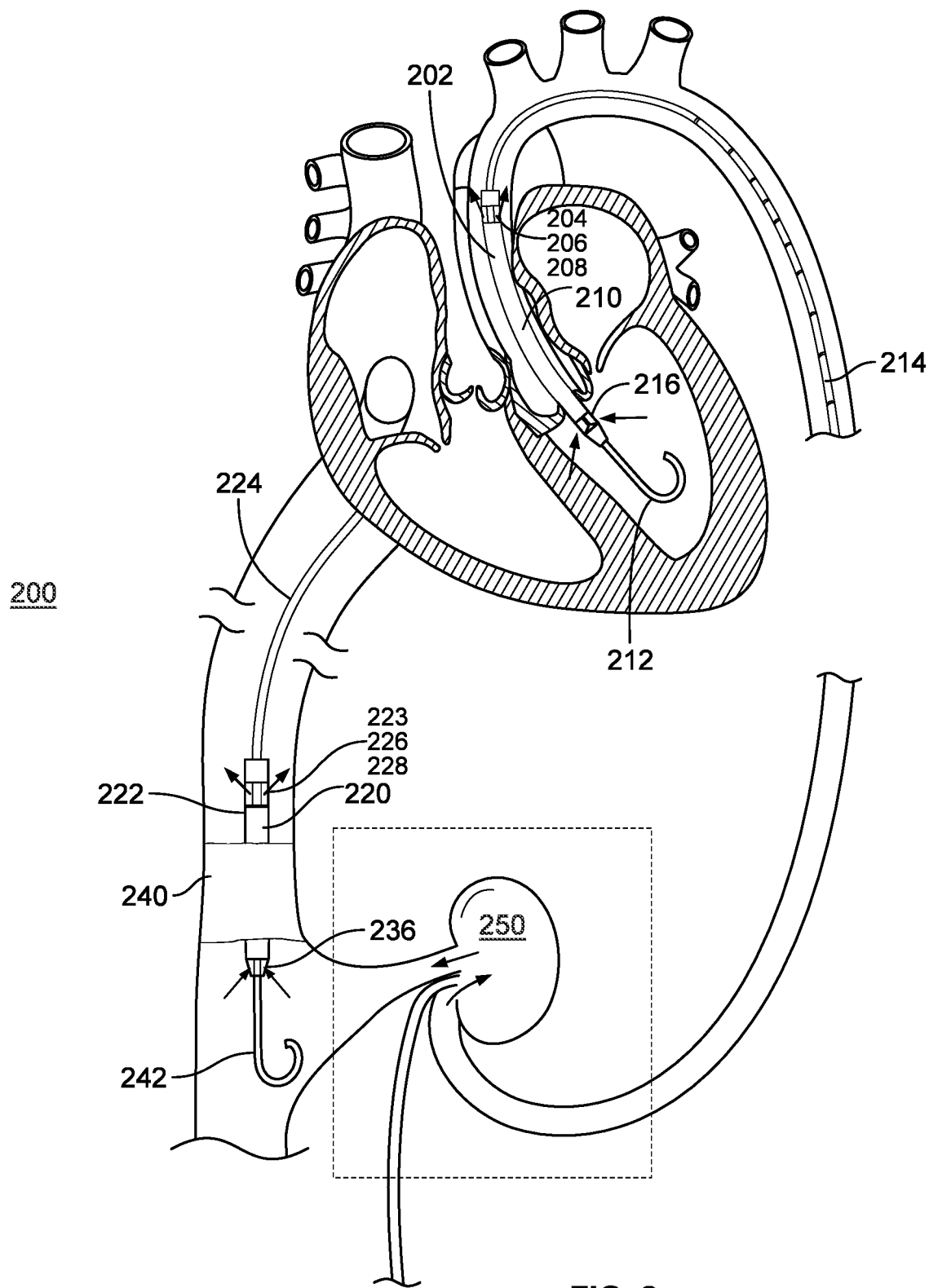
FIG. 2 shows an illustrative embodiment of the system disclosed herein.

FIG. 2 shows an illustrative embodiment of system 200, which is configured to provide either a similar or higher arterial pressure, similar or lower venous pressure, or a combination of both. A higher arterial pressure (input into an organ, e.g. a kidney) will result in an increased blood flow through the organ. For example, for a kidney, a higher arterial pressure will result in increased blood flow through the kidney, and in turn an increased renal urinary output. Similarly a lower venous pressure (at the organ output, e.g. at a kidney output) will result in an increased blood flow through the organ. For example, for a kidney, a higher arterial pressure will result in increased blood flow through the kidney, and in turn an increased renal urinary output. A combination of a higher arterial pressure (input into an organ, e.g. kidney) and lower venous pressure (at the organ output, e.g. kidney output) will result in a similar or greater increase in blood flow through the organ. When the organ is a kidney, the combination of higher arterial pressure and lower venous pressure will result in increased renal urinary output. Systems 200 comprises pump 202 and pump 222. For example pump 202 and 222 are Impella® pumps. Alternatively, pumps 202 and 222 are other mechanical circulatory assist devices, such as an expandable pump, intra-aortic balloon pump or an extracorporeal membrane oxygenation system (ECMO).

Pump 202 and Pump 222 control input and output into an organ, e.g. kidney 250 in FIG. 2. For example, kidney 250 may be the left kidney or the right kidney. In one example, the combination of pump 202 and pump 222 controls input and output into both kidneys. For example, operating one or both blood pumps changes a flow quantity and flow rate of blood through the organ, e.g. kidney. For example, operating one or both blood pumps increases a flow quantity and flow rate of blood through the kidney.

As shown in FIG. 2, pump 202 is a first blood pump with motor 204 and rotor 206 in housing 208, cannula 210, distal extension 212, and catheter 214. As shown in the example of FIG. 2, pump 202 is placed with distal extension 212 in the left ventricle, and rotor 206 and rotor housing 208 in the aorta. When operating, pump 202 draws blood through the inlet 216, through cannula 210 and out through housing 208 (also referred to as the rotor shroud), unloading the heart. Distal extension 212 acts to stabilize pump 202 in the ventricle. For example, distal extension 212 is a pigtail or j-shape. When operating, pump 202 unloads the left ventricle and increases pressure in the aorta, thereby increasing arterial pressure downstream. Pump 202 can operate at a range of speeds resulting in a range of flow rates and associated increases in aortic pressure. For example, the pump 202 is operated at a flow rate between about 1.5 L/min and 6 L/min. In one example, the pump 202 is operated at a flow rate of about 5 L/min. Pump 202 may be percutaneously inserted into a patient via the femoral artery, or via the subclavian vein.

As shown in FIG. 2, pump 222 is a second blood pump with motor 223 and rotor 226 in housing 228, cannula 220, distal extension 222242 and catheter 224. As shown in the example of FIG. 2, pump 222 is placed in the inferior vena cava. When operating, pump 222 draws blood through the inlet 236, through cannula 220 and out through rotor housing 228 (also referred to as the rotor shroud). Rotor housing 228 with rotor 226 is in the inferior vena cava, downstream of inlet 236, also in the inferior vena cava. In one example, e.g. as shown in FIG. 2, pump 222 includes distal extension 242 which stabilizes pump 222 in the inferior vena cava, or at a junction between the inferior vena cava and the renal vein. For example, distal extension 242 is a pigtail or j-shape. Pump 222 also includes anchoring mechanism 240, positioned on the cannula between inlet 236 and rotor housing 228 through which blood exits the pump. Anchoring mechanism 240 can both anchor the pump 222 at a desired position along the inferior vena cava and partially occlude the inferior vena cava to allow operation of pump 222 across the anchoring mechanism. For example, anchoring mechanism 240 anchors pump 222 between about 1-5 centimeters downstream of the renal vein. In another example, anchoring mechanism 240 anchors pump 222 between about 2-3 centimeters downstream of the renal vein. In one example, anchoring mechanism 240 is a balloon, which can be selectively inflated to at least partially occlude the inferior vena cava. For example, the size, shape, material and position of the balloon on the cannula 220 are selected to achieve different levels of occlusion in the inferior vena cava. In another example, anchoring mechanism 240 is an expand able cage. For example, anchoring mechanism 240 is a self-expanding cage (e.g. Nitinol) which is surrounded by a sheath for insertion, and self-expands once the sheath is removed in situ. The cage braces up against walls of the inferior vena cava and secures pump 222 in position. In on example, the cage may taper proximally and distally along the cannula, and be covered by a biocompatible cover material, to partially occlude the inferior vena cava.

Partial occlusion of the inferior vena cava, in combination with operation of pump 222 draws blood from a location within the inferior vena cava and/or renal vein, to a location downstream of the pump inlet 236, results in a pressure drop. The pressure drop can be measured as a pressure drop in the inferior vena cava upstream of pump 222 (e.g. proximate the renal vein), or a pressure drop in the renal vein. Alternatively, the pressure drop can be measured as a drop across the kidney between arterial pressure going into the kidney, and venous pressure coming out of the kidney (e.g., in the renal vein).

Pump 222 may be percutaneously inserted into a patient via the femoral artery, or via the subclavian vein. In one example, pump 222 and pump 202 are inserted through different percutaneous access points. Alternatively, pump 222 and pump 202 are inserted through a same percutaneous access point (e.g. subclavian vein).

In one example, each pump (e.g. pump 202, 222) includes a pressure sensor. For example, both pumps include an integrated pressure sensor, such as a differential pressure sensor, a piezoelectric pressure sensor, or an optical pressure sensor. In another example, both pumps include a separate pressure sensor, introduced on a pressure sensor wire, or a Swan-Ganz catheter. Alternatively, one of the pumps includes an integrated pressure sensor, whereas the other pump uses a separate pressure sensor. Pump 202 may include an integrated pressure sensor for detecting pressure. For example, pump 202 may include a differential pressure sensor, with one side of the sensor exposed to blood pressure on the outside of the inlet area, and another side of the sensor exposed to pressure of blood inside cannula 210. In this example, the sensor generates an electrical signal proportional to the difference between the two pressures, and the electrical signal is generated for display on a controller (e.g. an Automated Impella® controller). Alternatively, pump 202 may be introduced into the body of the patient, along with a Swan-Ganz catheter for measuring pressure. Similarly, pump 222 may include an integrated pressure sensor for detecting pressure. For example, pump 222 may include a differential pressure sensor, with one side of the sensor exposed to blood pressure on the outside of the inlet area, and another side of the sensor exposed to pressure of blood inside cannula 220. In this example, the sensor generates an electrical signal proportional to the difference between the two pressures, and the electrical signal is generated for display on a controller (e.g. an Automated Impella® controller). Alternatively, pump 222 may be introduced into the body of the patient along with a Swan-Ganz catheter for measuring pressure.

Each pump (e.g. pump 202 and 222) may be connected to a controller, e.g. an Automated Impella Controller®, which receives data from the pump and the sensor associated with the pump (e.g. either an integrated sensor or a separate sensor), and generates for display to the user (e.g. a medical professional) information on cardiac output, and/or renal output. As described below in relation to the example of FIG. 3, information from the controller is used to determine whether and when to stop operation of one or more pumps.

As described below in relation to FIG. 3, by operating pump 222 while pump 202 is operating, both the input arterial pressure to the kidney 250 and the output venous pressure from the kidney 250 can be adjusted. At least one advantage of this dual-pump operation is the ability to both increase the cardiac output and arterial pressure input to the kidney 250, and/or to decrease the venous pressure out of the kidney 250. Accordingly, operating pump 202 while pump 222 is operating increases blood flow to the kidney, and increases the amount of humoral factors reaching the kidney. Operating pump 222 while pump 202 is operating increases blood flow out of the kidney. At least one advantage of this dual-pump operation is the ability to increase urinary output and clear any stress factors, e.g. including stress factors resulting from surgery.

FIG. 3 shows an illustrative method 300 for improving kidney function. At step 302, a first blood pump (e.g. pump 202 of FIG. 2) is inserted into the patient's heart. At step 304, the first blood pump is operated so as to increase aortic pressure. At step 306, a second blood pump (e.g. pump 222 of FIG. 2) is inserted into the patient's inferior vena cava. After the second blood pump is inserted, an anchoring mechanism is deployed (e.g. anchoring mechanism 240 of FIG. 2). For example, the anchoring mechanism is a balloon surrounding a portion of the pump cannula (e.g. cannula 220 of pump 222 in FIG. 2). In this example, the balloon surrounding the portion of the pump is inflated, such that it anchors the pump in the inferior vena cava and partially occludes the inferior vena cava. At step 308, the second blood pump is operated while the first blood pump is operating. At step 312, the system determines whether a target renal parameter (e.g. blood pressure drop in the renal vein) has been achieved at a location in the patient's renal vein or inferior vena cava. If the determination at step 312 is that the target renal parameter (e.g. blood pressure drop in the renal vein) has been achieved, operation of the second blood pump can be stopped (step 314). If the determination at step 312 is that the target renal parameter (e.g. blood pressure drop in the renal vein) has not been achieved, a second determination is made as to whether to adjust operation of the first blood pump, and/or adjust operation of the second blood pump (step 310). For example, a speed of the first blood pump (e.g. pump 202 of FIG. 2) can be modified (e.g. increased or decreased) independently of a speed of the second blood pump. In one example, the speed of the first blood pump is increased by about 1 L/min. Alternatively, the speed of the first blood pump is increased by about 2 L/min. Similarly, a speed of the second blood pump (e.g. pump 222 of FIG. 2) can be modified (e.g. increased or decreased) independently of a speed of the first blood pump. In another example, the speed of both the first blood pump and second blood pump can be increased. If the determination at step 310 is that no adjustment is necessary, the method returns to a determination of whether target renal parameter has been achieved (step 312). For example, the target renal parameter may be a target pressure drop in pressure in the renal vein, or a target pressure drop across the kidney. For example, the first and second blood pump may have to be operated for a longer period of time to achieve an effect on either arterial pressure, venous pressure, or both. Instead if the determination at step 310 is that adjustment to operation of either or both of the first blood pump and the second blood pump is required, the method returns to step 308 where both first and second blood pumps are operated simultaneously.

For example, pump controllers (e.g. controllers of pump 222 and/or pump 202 of FIG. 2) are configured to operate one or both assist devices (e.g. pump 222 and/or pump 202 of FIG. 2) at respective rates so as to increases blood flow from the heart and stimulate production of at least one humoral factor that binds to a kidney receptor or another organ receptor to stimulate and/or modulate urine production and urinary fluid composition from the kidneys. In one example, as discussed above in relation to FIG. 2, both pumps (pump 222 and pump 202) are connected to a single controller. The controller(s) can receive data regarding a renal parameter. For example, the renal parameter is pressure drop at the outlet of the kidney. Alternatively, the renal parameter is pressure drop across the organ. As another example, the renal parameter is creatinine level or ANP concentration in the blood. In one example, the controllers of both pumps communicate with one another.

In one example, the controller(s) can also compare the renal parameter with threshold values of the renal parameter. For example, the controller(s) can compare continuously in near real-time the renal parameter to a threshold value. Alternatively, the controller(s) can compare periodically. Threshold values may be input by a user. Alternatively threshold values may be retrieved by the controller from a database. For example, the database is a remote database using known clinical data for target renal parameter values. In one example, the controller(s) is configured to generate for display an indicator that the threshold value for the renal parameter has been reached. For example, the controller(s) may generate an alarm. In another example, the controller(s) send a message to a physician. In one example, the physician can turn off one or more of the pump based on the renal parameter monitoring. For example, the physician can turn off pump 222 while maintaining operation of pump 202 once the renal parameter (e.g. pressure in the renal vein) has reached a threshold value. In another example, the controller(s) detects that the renal parameter has reached a threshold value, and automatically turns off one or more pumps. At least one advantage of being able to determine when to turn off one more pumps is the ability safely wean the patient off support, and the ability to improve organ (e.g. kidney function) without damaging the organ (e.g. kidney) by subjecting it to high blood pressure for longer than necessary.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system for intracardiac heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method for modulating kidney function in a patient, comprising the steps of:

inserting a first blood pump into a heart of a patient;
operating the first blood pump in the heart of the patient so as to increase aortic pressure;
inserting a second blood pump into an inferior vena cava of the patient; and
operating the second blood pump in the inferior vena cava of the patient and the first blood pump in the heart of the patient such that while the second blood pump is operating, the first blood pump is also operating; and
adjusting operation of at least one of the first blood pump and the second blood pump to achieve a target pressure drop at a location in a renal vein or the inferior vena cava of the patient.

2. The method of claim 1, wherein operating the second blood pump includes pumping the second blood pump while the first blood pump is pumping.

3. The method of claim 2, wherein operating the first blood pump maintains or increases arterial pressure in a renal artery of the patient.

4. The method of claim 3, wherein operating the second blood pump maintains or decreases renal vein pressure.

5. The method of claim 1, comprising operating the first blood pump to increase arterial pressure, and operating the second blood pump to decrease renal vein pressure.

6. The method of claim 2, wherein the location is a vascular junction where the renal vein and the inferior vena cava of the patient connect.

7. The method of claim 2, wherein the target pressure drop increases blood flow through a kidney of the patient and increases kidney output.

8. The method of claim 7, wherein the target pressure drop is between about 4 mmHg and about 8 mmHg.

9. The method of claim 7, wherein the target pressure drop is between about 5 mmHg and about 7 mmHg.

10. The method of claim 2, wherein the target pressure drop corresponds to a blood pressure drop across a kidney of the patient.

11. The method of claim 2, wherein combined operation of the first blood pump and the second blood pump flows humoral factors to kidney receptors of the patient to stimulate an increase in urine exiting a kidney of the patient.

12. The method of claim 1, wherein the first blood pump comprises:
a pump motor;
a pump housing distal of the pump motor, the pump housing surrounding a rotor;
and a cannula extending distal of the pump housing; and
an atraumatic extension extending distally from the cannula.

13. The method of claim 1, wherein the second blood pump comprises:
a pump motor;
a pump housing distal of the pump motor, the pump housing surrounding a rotor; and
a cannula extending distal of the pump housing.

14. The method of claim 13, wherein the second blood pump further comprises an atraumatic extension extending distally from the cannula.

15. The method of claim 14, wherein the second blood pump is positioned inside the inferior vena cava of the patient such that a distal tip of the atraumatic extension of the second blood pump extends to a location adjacent to an outlet of the renal vein of the patient.

16. The method of claim 1, wherein the first blood pump is inserted into a ventricle of the heart of the patient.

17. The method of claim 1, wherein kidney function is modulated during or after surgery.

18. The method of claim 1, further comprising:
receiving, by a controller, an arterial pressure from the first blood pump, and a venous pressure from the second blood pump,
determining, by the controller, a pressure drop in the renal vein is not at the target pressure drop in the renal vein; and
adjusting, by the controller, operation of at least one of the first blood pump and the second blood pump to achieve the target pressure drop in the renal vein.

* * * * *

UNITED STATES PATENT AND TRADEMARK OFFICE
CERTIFICATE OF CORRECTION

PATENT NO. : 11,298,519 B2
APPLICATION NO. : 16/406896
DATED : April 12, 2022
INVENTOR(S) : Noam Josephy et al.

It is certified that error appears in the above-identified patent and that said Letters Patent is hereby corrected as shown below:

In the Specification

Column 8, Line 40:
New reads: "222242"; should read -- 242, --

Signed and Sealed this
Ninth Day of August, 2022

Katherine Kelly Vidal
*Director of the United States Patent and Trademark Office*